United States Patent
Liu et al.

(10) Patent No.: US 10,508,755 B2
(45) Date of Patent: Dec. 17, 2019

(54) FLUID DELIVERY DEVICE WITH HYDROPHOBIC SURFACE

(71) Applicant: INTERNATIONAL BUSINESS MACHINES CORPORATION, Armonk, NY (US)

(72) Inventors: Yang Liu, Ossining, NY (US); Steven L. Wright, Cortlandt Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/656,126

(22) Filed: Jul. 21, 2017

(65) Prior Publication Data

US 2019/0024823 A1 Jan. 24, 2019

(51) Int. Cl.
*F16K 99/00* (2006.01)
*A61M 31/00* (2006.01)
(Continued)

(52) U.S. Cl.
CPC ...... *F16K 99/0044* (2013.01); *A61B 5/14539* (2013.01); *A61B 5/6861* (2013.01);
(Continued)

(58) Field of Classification Search
CPC ............. F16K 99/0044; F16K 99/0015; F16K 2099/0088; A61M 35/00; A61M 2205/50;
(Continued)

(56) References Cited

U.S. PATENT DOCUMENTS

| 5,366,454 A | 11/1994 | Currie et al. |
| 5,797,898 A * | 8/1998 | Santini, Jr. ........... A61K 9/0009 604/890.1 |

(Continued)

FOREIGN PATENT DOCUMENTS

| EP | 2128987 A1 | 2/2009 |
| WO | 9509670 A1 | 4/1995 |

(Continued)

OTHER PUBLICATIONS

Farra et al., "First-in-Human Testing of a Wirelessly Controlled Drug Delivery Microchip", Sci Transl Med vol. 4, Issue 122 122ra21 (Feb. 22, 2012); DOI: 10.1126/scitranslmed.3003276; downloaded from tm.sciencemag.org; on Aug. 15, 2014; 11 pgs.
(Continued)

*Primary Examiner* — Nathan R Price
*Assistant Examiner* — Mark Alan Igel
(74) *Attorney, Agent, or Firm* — Cantor Colburn LLP; Vazken Alexanian

(57) ABSTRACT

Embodiments of the present invention are directed to a liquid delivery apparatus. A non-limiting example of the apparatus includes a substrate including a cavity formed in a surface of the substrate. The apparatus can also include a membrane disposed on the surface of the substrate covering an opening of the cavity. The apparatus can also include a hydrophobic layer disposed on the membrane. The apparatus can also include a seal disposed between the membrane and the substrate, wherein the seal surrounds the opening of the cavity. The apparatus can also include an electrode layer coupled to the membrane.

12 Claims, 10 Drawing Sheets

(51) Int. Cl.
*H01M 2/36* (2006.01)
*A61B 5/00* (2006.01)
*A61K 9/00* (2006.01)
*A61B 5/145* (2006.01)
*A61M 35/00* (2006.01)

(52) U.S. Cl.
CPC ......... *A61K 9/0024* (2013.01); *A61M 31/002* (2013.01); *F16K 99/0015* (2013.01); *H01M 2/361* (2013.01); *A61M 35/00* (2013.01); *A61M 35/10* (2019.05); *A61M 2205/3303* (2013.01); *A61M 2205/50* (2013.01); *A61M 2205/52* (2013.01); *F16K 2099/0088* (2013.01); *H01M 2220/30* (2013.01)

(58) Field of Classification Search
CPC ..... A61M 2205/52; A61M 2205/3303; H01M 2/361; H01M 2220/30
USPC ........................................................ 604/503
See application file for complete search history.

(56) References Cited

U.S. PATENT DOCUMENTS

| | | | |
|---|---|---|---|
| 6,527,762 B1* | 3/2003 | Santini, Jr. ............ | A61K 9/0009 216/2 |
| 6,953,455 B2* | 10/2005 | Cho ..................... | A61K 9/0024 604/890.1 |
| 7,455,667 B2 | 11/2008 | Uhland et al. | |
| 7,473,248 B2 | 1/2009 | Santini, Jr. et al. | |
| 7,510,551 B2 | 3/2009 | Uhland et al. | |
| 8,211,092 B2 | 7/2012 | Uhland et al. | |
| 8,830,561 B2* | 9/2014 | Zang .................... | C09K 19/544 359/296 |
| 2002/0103139 A1 | 8/2002 | Weisspapir et al. | |
| 2002/0107470 A1* | 8/2002 | Richards ............. | A61K 9/0009 604/20 |
| 2002/0151776 A1* | 10/2002 | Shawgo ................ | A61B 5/145 600/345 |
| 2002/0187260 A1* | 12/2002 | Sheppard, Jr. ....... | A61K 9/0009 427/248.1 |
| 2004/0043042 A1* | 3/2004 | Johnson ................ | F26B 5/06 424/400 |
| 2004/0166140 A1* | 8/2004 | Santini, Jr. .......... | A61K 9/0009 424/424 |
| 2004/0224003 A1 | 11/2004 | Schultz | |
| 2010/0004583 A1 | 1/2010 | Panos et al. | |
| 2011/0196347 A1* | 8/2011 | Atansoska ........... | A61M 5/142 604/890.1 |
| 2012/0237763 A1* | 9/2012 | Kluge .................. | A61M 35/00 428/336 |
| 2013/0034610 A1 | 2/2013 | Dai et al. | |
| 2014/0330244 A1* | 11/2014 | Hyde .................... | A61B 5/076 604/503 |
| 2015/0126913 A1* | 5/2015 | Jurna .................... | A61B 18/12 601/9 |
| 2016/0074323 A1 | 3/2016 | Chey et al. | |
| 2017/0119960 A1* | 5/2017 | Dang ................. | A61M 5/14276 |
| 2019/0015257 A1* | 1/2019 | Vickery ................ | A61F 13/00 |

FOREIGN PATENT DOCUMENTS

| | | |
|---|---|---|
| WO | 2005009480 A2 | 2/2005 |
| WO | 2010002962 A3 | 1/2010 |

OTHER PUBLICATIONS

Maloney, et al., "Electrothermally activated microchips for implantable drug delivery and biosensing", Journal of Controlled Release 109 (2005), pp. 244-255.

Lu, Jie, et al., "Mesoporous silica nanoparticles as a delivery system for hydrophobic anticancer drugs", small 3.8 (2007): 1341-1346.

* cited by examiner

FLUID DELIVERY DEVICE WITH HYDROPHOBIC SURFACE

BACKGROUND

The present invention generally relates to miniaturized delivery devices and related methods, and more specifically to liquid delivery devices with hydrophobic surfaces and related methodologies.

Micro-scale delivery devices can be useful in a variety of applications. Such delivery devices can include an array of micro-scale reservoirs filled with small amounts of material such as liquids or powders. The reservoirs are sealed with material and can provide controlled delivery of the material, for example, by rupture or melting of a metal membrane. Such micro-scale delivery devices can provide independent and controlled release of materials in individual reservoirs and can, for example, be useful in drug delivery applications.

In some applications, achieving the desired size of the micro-scale delivery device can place severe constraints on energy storage and power delivery. For example, smaller sizes of implantable and wearable drug delivery devices can be preferred for patient comfort and privacy. Reservoir release of the material, however, requires energy and, moreover, can be subject to major sources of energy loss through thermal conduction within the device structure. Reservoirs containing liquids, for instance, can experience undesirably high thermal conduction. Thus, there remains a need to minimize energy required for reservoir release.

SUMMARY

Embodiments of the present invention are directed to a liquid delivery apparatus. A non-limiting example of the apparatus includes a first substrate including a reservoir formed in the first substrate. The apparatus can also include a membrane disposed on the surface of the first substrate covering an opening of the reservoir. The membrane can include, in some embodiments of the invention, a metal layer, an electrically-insulating dielectric layer, or a combination of metallic and insulating structures. The apparatus can also include a second substrate bonded to the first substrate, wherein the second substrate includes a reservoir seal. The apparatus can also include a hydrophobic layer disposed on an inside surface of the membrane. The apparatus can also include an electrode in electrical contact with the membrane. Such embodiments can provide activation by melting or fracturing the membrane and provide automated delivery of a liquid with minimized energy losses due to thermal conduction of the liquids.

Embodiments of the present invention are directed to a liquid delivery apparatus. A non-limiting example of the apparatus includes a substrate including a cavity formed in a surface of the substrate. The apparatus can also include a membrane connected to a hinged structure. The apparatus can also include a hydrophobic layer disposed on the membrane. The apparatus can also include a seal disposed between the membrane and the substrate, wherein the seal surrounds the opening of the cavity. Such embodiments can provide device activation by melting or breaking the seal, providing automated delivery of a liquid with reduced release of membrane or seal debris.

Embodiments of the present invention are directed to an electronic delivery device. A non-limiting example of the device includes a dispensing array including a plurality of reservoirs. The dispensing array can include a cavity, a membrane covering an opening of the cavity, and a hydrophobic layer disposed on the membrane. The device can also include a microprocessor in communication with the dispensing array. The device can also include a wireless receiver in communication with the microprocessor. Such embodiments can provide energy efficient remote release of fluids from a dispensing array in a miniaturized delivery device.

Embodiments of the present invention are directed to a method of delivering liquids. A non-limiting example of delivering the liquids includes forming a hydrophobic liner on a release membrane covering a delivery structure reservoir. The method also includes depositing a liquid in the reservoir. The method also includes sealing the reservoir with a hydrophilic layer. The method also includes providing an electric current to the release membrane to dispense the liquid. Such embodiments can preserve integrity of liquids for automated release in electronic delivery devices.

Embodiments of the present invention are directed to a computer program product for delivery of liquids. The computer program product can include a computer readable storage medium having program instructions embodied therewith, wherein the instructions are executable by a processor to perform a method. A non-limiting example of the method includes receiving a signal from a sensor concerning a local environmental condition. The method can also include sending, based at least in part upon the signal, an electric current to a release membrane lined with a hydrophobic liner, wherein the release membrane covers a delivery structure reservoir. The method can also include rupturing the membrane with the electric current.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
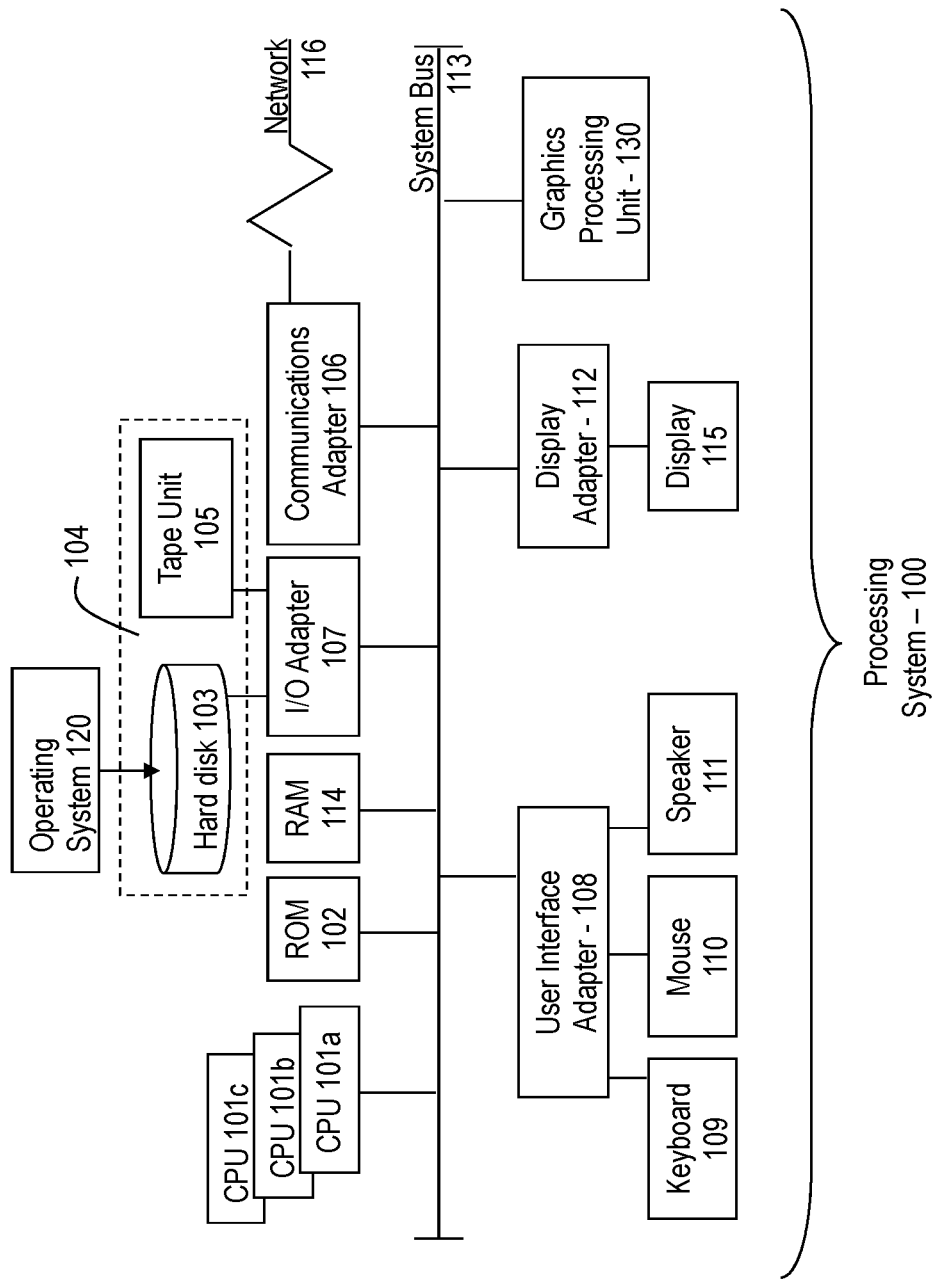
FIG. 1 depicts a block diagram illustrating one example of a processing system according to one or more embodiments of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Turning now to an overview of technologies that are more specifically relevant to aspects of the invention, digital delivery devices can be desirable in applications that can benefit from precise scheduling and/or release of precise amounts of material in an automatic fashion. For instance, in drug delivery applications, digital delivery devices can include a plurality of reservoirs that can be independently and/or remotely released according to a precise dosage and schedule. In some cases, including pharmaceutical and non-pharmaceutical applications, digital delivery devices can be used to provide release of an agent for precise or automated initiation or termination of a chemical reaction. For example, in microbattery applications, digital release of an electrolyte from a reservoir can activate the microbattery remotely. In another application, an array of biosensors, contained in a backplane, are configured to respond to specific biomarkers following chemical activation. Prior to use, the biosensor surfaces can be cleaned. The individual biosensors can be sealed and protected by a membrane, and each biosensor can be in close proximity to a reservoir containing a liquid chemical that activates the biosensor surface for analyte biomarker detection. Upon application of an activation signal, the membrane containing the activation chemical reservoir and the membrane sealing the biosensor are both opened. In some cases, moreover, digital delivery devices can be interfaced to sensor systems to provide an automatic closed-loop drug delivery system.

The ability to remotely release materials from digital delivery devices makes them potentially useful in implantable or wearable devices. For example, treatment of some medical conditions can call for administration of agents that are not suitable or optimal for oral administration or for delivery of agents according to a precise dosage and schedule. For such applications, drug delivery implants have potential to provide administration of agents according to a precise schedule with minimal involvement of a patient or health care provider. In addition to implanted systems, digital delivery devices could provide similar delivery benefits in wearable (e.g., transdermal, transmucosal, etc.) systems, such as in adhesive patch systems.

Inclusion of digital delivery devices in applications in which device size is important, such as in implantable or wearable devices, can pose challenges in system design. Aside from any patient and health care provider preferences for small devices for patient comfort, there can be physical limitations on the size of devices that can be implanted into or worn by the patient. As such, smaller device volumes can significantly constrain energy storage and power delivery. Minimizing the energy required for reservoir release can improve device design and performance.

Thermal conduction within the device structure can be a major source of energy loss in digital delivery devices. For instance, reservoirs including liquids can experience high thermal conduction.

Conventional digital delivery devices can include a destructible metal membrane covering a reservoir. To obtain release of an agent from the reservoir, the membrane can be activated by providing an electric current sufficient to rupture or melt the membrane and, thereby, expose the reservoir opening to the surrounding environment. However, liquids are good thermal conductors. Prior to rupture or melt of the membrane, liquid in the reservoir or cavity that is in contact with the membrane will draw additional energy from the system. Energy drawn from the system can, moreover, vaporize the liquid that is in contact with the membrane. Such vaporization can not only require additional heat but can also potentially degrade or damage temperature sensitive agents in the reservoir.

Some conventional digital delivery devices can include releasable membranes, such membranes attached to the device body via a hinge. Upon activation through application of energy to the system, the membrane can partially release from the structure, exposing liquid in a reservoir or cavity to the surrounding environment. For reasons similar to those noted above, liquids in contact with the sealing rings of such devices can increase the energy needed to open the membrane.

Conventional methods of reducing liquid reservoir energy inefficiencies can include lyophilizing intended reservoir materials to reduce and/or eliminate reservoir liquids. Lyophilization (freeze drying) is a process in which water is removed from a sample by freezing a solution of interest and sublimating the water from the frozen solution under low pressure, leaving behind a dried or powdered sample. However, lyophilization, in addition to requiring additional expense and processing steps, can be unsuitable for certain compounds and, further, can require additional reconstitution steps before administering the desired agent to its target. Moreover, lyophilization can often require large batch processing to be cost-effective. A need remains to reduce thermal conduction in digital delivery systems, in particular in systems that include liquid reservoir materials.

Turning now to an overview of the aspects of the invention, one or more embodiments of the invention address the above-described shortcomings of the prior art by providing a hydrophobic layer on the release membrane of a digital delivery device. In some embodiments of the invention, a reservoir is sealed at an end opposite the membrane and hydrophobic layer with a second substrate. The second substrate can include, in some embodiments of the invention, a hydrophilic surface. Such embodiments of the invention can draw the liquid to the hydrophilic surface and away from the membrane The above-described aspects of the invention address the shortcomings of the prior art by reducing thermal conduction in the device structure by repelling liquid substances from the reservoir or cavity away from the membrane. In some embodiments of the invention, liquid in the reservoir is drawn to a hydrophilic surface opposite the hydrophobic layer and the membrane. In some embodiments of the invention, the hydrophobic layer provides formation of an air pocket between a reservoir fluid surface and the membrane, in which the air pocket provides thermal insulation and improved thermal properties.

Referring to FIG. 1, there is shown an embodiment of a processing system 100 for implementing the teachings herein. In this embodiment of the invention, the system 100 has one or more central processing units (processors) 101a, 101b, 101c, etc. (collectively or generically referred to as processor(s) 101). In one embodiment of the invention, each processor 101 can include a reduced instruction set computer (RISC) microprocessor. Processors 101 are coupled to system memory 114 and various other components via a system bus 113. Read only memory (ROM) 102 is coupled to the system bus 113 and can include a basic input/output system (BIOS), which controls certain basic functions of system 100.

FIG. 1 further depicts an input/output (I/O) adapter 107 and a network adapter 106 coupled to the system bus 113. I/O adapter 107 can be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 can be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which can include a graphics adapter to improve the performance of graphics intensive applications and a video controller. In one embodiment of the invention, adapters 107, 106, and 112 can be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which can include, for example, a Super I/O chip integrating multiple device adapters into a single integrated circuit.

In exemplary embodiments of the invention, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing, and has a highly parallel structure that makes it more effective than general-purpose CPUs for algorithms where processing of large blocks of data is done in parallel.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment of the invention, a portion of system memory 114 and mass storage 104 collectively store an operating system such as the AIX® operating system from IBM Corporation to coordinate the functions of the various components shown in FIG. 1.

Figure 2A:
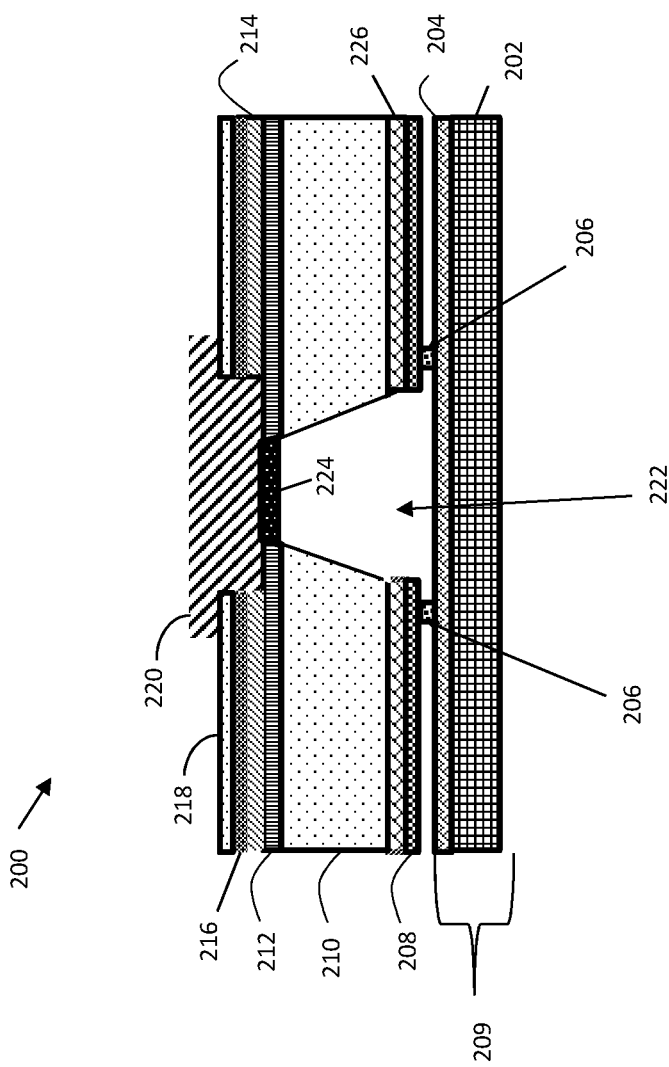
FIG. 2A depicts an exemplary system according to one or more embodiments of the present invention.

Turning now to a more detailed description of aspects of the present invention, FIG. 2A depicts a hydrophobic delivery system 200 according to embodiments of the invention. The system 200 includes a first substrate 210 including a reservoir 222 formed in the surface of the substrate 210. The system 200 can include a first sacrificial layer 212 on top of the first substrate 210. The sacrificial layer 212 can include, for example, silicon nitride (SiN) or silicon dioxide ($SiO_2$). The system 200 can include an electrode layer including multilayer metal stack including a plurality of metal layers 214, 216, 218. The system 200 can also include a membrane 220 in contact with one or more of the metal layers 214, 216, 218 and covering an opening of the reservoir 220. The membrane 220 can include a metal film, for example a metal film with a thickness of about 1 micron. The membrane 220 can include a metal that can be ruptured or melted upon activation and can include, for instance, gold, aluminum, indium, or a reactive material consisting of a stack of metal layers such a nickel and aluminum, or aluminum and palladium. The membrane 220 can also include electrically-insulating dielectric materials such as silicon dioxide ($SiO_2$), silicon nitride ($SiN_x$), or polymer materials. In some embodiments of the invention, the membrane 220 includes a hydrophobic layer 224 on a surface facing the cavity 222. The system 200 can include a second sacrificial layer 226 on the bottom of the substrate 210. The second sacrificial layer 226 can include the same material or a different material than the first sacrificial layer 212, such as $SiN_x$ or $SiO_2$. The system 200 can also include a sealing layer 208 and reservoir seal 206. The sealing layer 208 and reservoir seal 206 can include a low melting point material, such as a metal coated polymer layer including indium (In). The reservoir seal 206 can be coupled to a second substrate 209 including a biocompatible layer 202 coated with a metal compatible layer 204. In some embodiments of the invention, the reservoir seal provides a permanent and/or irreversible seal to the reservoir.

The sealing layer 208 and seal 206 can surround an opening of the cavity 222 and can be configured to enclose the cavity 222 and retain a substance within the cavity. While only one cavity 222 is shown for illustrative purposes, it is to be understood that the substrate 210 can be formed with an array of cavities, including for instance hundreds of cavities that serve as reservoirs for holding the same type or a combination of different types of deliverable substances.

The number of metal layers can vary dependent upon the desired application of the system. For example, a system including a higher number of reservoir types or with a relatively complex release schedule can include a higher number of metal layers than a system including fewer reservoir types or a simpler release schedule. The metal layers 214, 216, 218, can include metallic material such as copper, gold, platinum, or titanium and can be in the form of metal layers or in the form of patterned layers including metallic electrode elements, including copper, gold, platinum, or titanium, formed in one or more silicon dioxide layers. In some embodiments of the invention, electrodes are in electrical contact with the membrane, for instance providing electric current to heat the membrane or a portion of the membrane. The multilayer metal stack can be configured to locally heat a portion of the membrane 220.

The cavity 222 can have a diameter suitable to house a liquid in a quantity sufficient for the desired application, such as about 1 to about 100 nanoliters (nL), or about 10 to about 50 nL of fluid. For example, the cavity 222 can have a diameter ranging from about 100 microns to about 1 millimeter (mm) and can have a depth of about 100 to about 500 microns.

The biocompatible layer 202 includes a biocompatible substrate, such as a substrate including polydimethylsiloxane (PDMS), silicon, glass, polyimide, such as KAPTON®, or a biocompatible cement. The metal compatible layer 204 can include a material that can be coupled to the seal 206. In some embodiments of the invention, the metal compatible layer 204 includes gold.

The hydrophobic layer 224 can be deposited, grown or formed on the structure, for instance by plasma deposition, surface treatment, coating or nano-coating, electrodeposition. The hydrophobic layer 224 can include materials with a hydrophobicity sufficient to repel a desired aqueous material in the reservoir. The hydrophobic layer can include for example fluorocarbons, such as teflon, teflon-like materials, or other plasma deposited hydrophobic fluorinated thin films; micro-structured polymers, such as PDMS or SU-8; nano-coatings such as coatings including silica particles, polytetrafluoroethylene (PTFE), or alumina particles; electrodeposited metal films, such as porous electrodeposited metal films, for instance porous gold film; oxides and oxide composites, such as manganese oxide polystyrene ($MnO_2$/PS) nano-composite or zinc oxide polystyrene (ZnO/PS) nano-composite; precipitated calcium carbonate, carbon nanotubes; or patterned films, such as pillar and/or groove structured films. In some embodiments of the invention, the hydrophobic layer 224 lines only the membrane 220. In some embodiments of the invention, the hydrophobic layer 224 lines the membrane and at least part of the cavity, such as the cavity walls adjacent to the membrane. The hydrophobic layer can have a thickness of about 5 Angstrom (Å) to about 1 micron. In some embodiments of the invention, at least a portion of the membrane includes an electrically-insulating film.

Figure 2B:
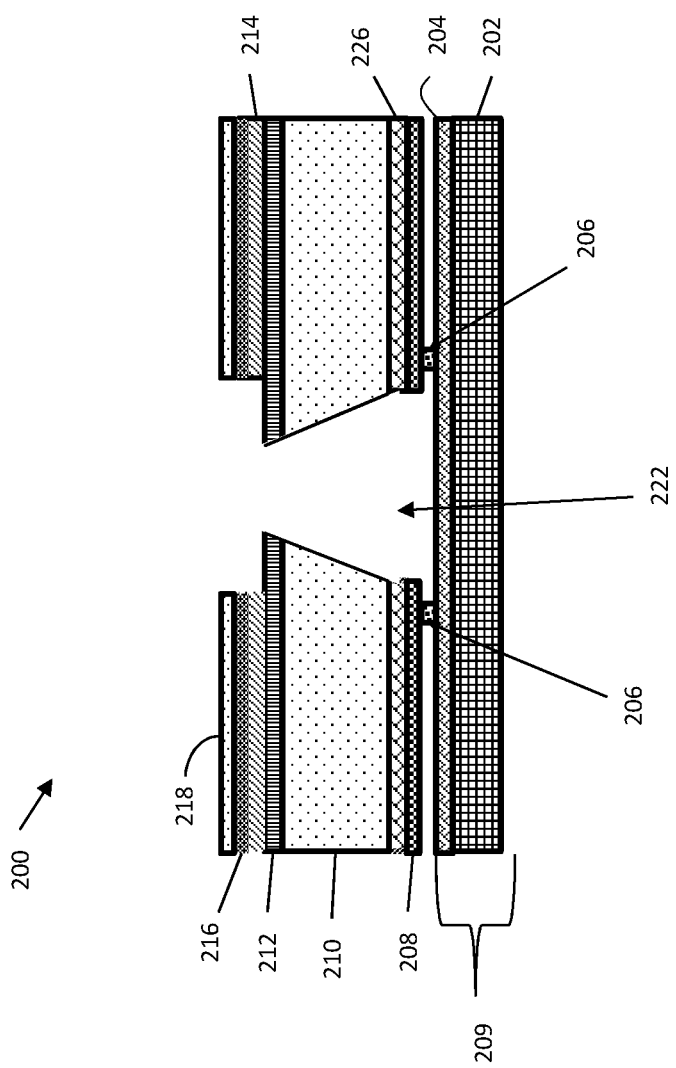
FIG. 2B depicts another view of the exemplary system of FIG. 2A according to one or more embodiments of the present invention.

FIG. 2B depicts the exemplary hydrophobic delivery system 200 of FIG. 2A after activation according to some embodiments of the invention. After activation, membrane 220 and hydrophobic layer 224 are removed from the device, for instance by rupture or melt of the membrane upon stimulation with an electric current, and the cavity 222 is accessible by the local environment.

Hydrophobic delivery systems according to embodiments of the invention can be fabricated using standard materials and semiconductor fabrication processes, including Micro-Electro-Mechanical (MEMS) technology, Back End Of the Line (BEOL) technology, photolithography, wafer bonding, wafer thinning, and wafer transfer processes, for example. In some embodiments of the invention, materials used for constructing delivery devices include materials that are biocompatible or that can otherwise be made biocompatible by coating with suitable biocompatible materials.

For example, the substrate 210 can be formed using any standard semiconductor material such as silicon, or glass, ceramic, etc., which can be micro-machined or etched using standard etching processes (e.g. anisotropic wet chemical etching or deep reactive ion etching (DRIE)) and wafer thinning processes, for example. The substrate 210 can be formed using a biocompatible material, such as silicon, which is not permeable to the liquid contents contained in the etched cavities. The dimensions and shape of the cavity 222 and the number of cavities formed in the substrate 210 will vary depending on the application. In one embodiment of the invention, the cavities 222 are circular-shaped cavities that are formed in a silicon substrate using a deep RIE process. In other embodiments of the invention, the cavities can be in the shape of truncated, four-sided pyramids formed by anisotropic wet etch of (100)-oriented silicon.

In some embodiments of the invention, a cavity 222 within a substrate can be filled with liquid prior to sealing the cavity 222. For example, a cavity 222 can be filled with a liquid prior to coupling the reservoir seal 206 to a second substrate 209. In such embodiments of the invention, the sealing process implemented is one that does not adversely affect or otherwise disturb or degrade the deliverable substance filled within the cavity 222.

In some embodiments of the invention, hydrophobic delivery systems can include sensors. Sensors can include any sensing apparatus that useful in a miniaturized or automated delivery system. Sensors can include, for example, pH sensors, ionic sensors, heart rate sensors, blood pressure sensors, flow sensors, humidity sensors, action potential sensors, local field potential sensors, chemical sensors, such as nucleic acid sensors, protein sensors, exosome sensors, glucose sensors, or neurotransmitter specific sensors, optical sensors, or acoustic sensors.

Figure 3A:
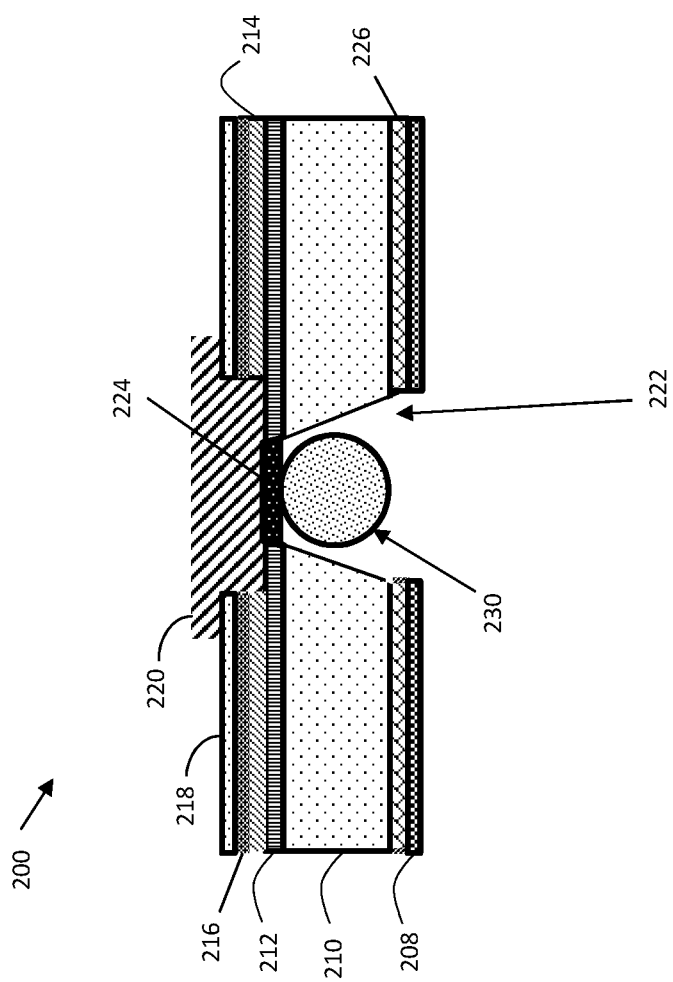
FIG. 3A depicts an exemplary system according to one or more embodiments of the present invention.

FIG. 3A depicts the exemplary hydrophobic delivery system 200 of FIG. 2A in an exemplary step of the process of filling the device with a fluid. The system 200 includes a substrate 210 including a cavity 222 formed in the surface of the substrate 210. The system 200 can include a first sacrificial layer 212 on top of the substrate 210. The sacrificial layer 212 can include, for example, silicon nitride (SiN) or silicon dioxide ($SiO_2$). The system 200 can include a multilayer metal stack including a plurality of metal layers 214, 216, 218. The system 200 can also include a membrane 220 in contact with one or more of the metal layers 214, 216, 218 and covering the cavity 220. The membrane 220 can include a thin metal film, for example a metal film with a thickness of about 1 micron. The membrane 220 includes a metal that can be ruptured, melted, or partially melted upon activation. Activation of the system to release the contents of a reservoir can include providing a high density current flow through the membrane 220, for instance by way of one or more electrodes in contact with the membrane. The membrane 220 can include, for instance, aluminum, gold, or a reactive material such as layered structure of aluminum and palladium. A hydrophobic layer 224 lines a face of the membrane in the cavity 220. A drop of solution 230 can be deposited in the cavity. As is shown in FIG. 3A, the hydrophobic layer 224 can repel the solution 230 so as to minimize its contact with the membrane 220 and hydrophobic layer 224, for example by forming a bead.

Figure 3B:
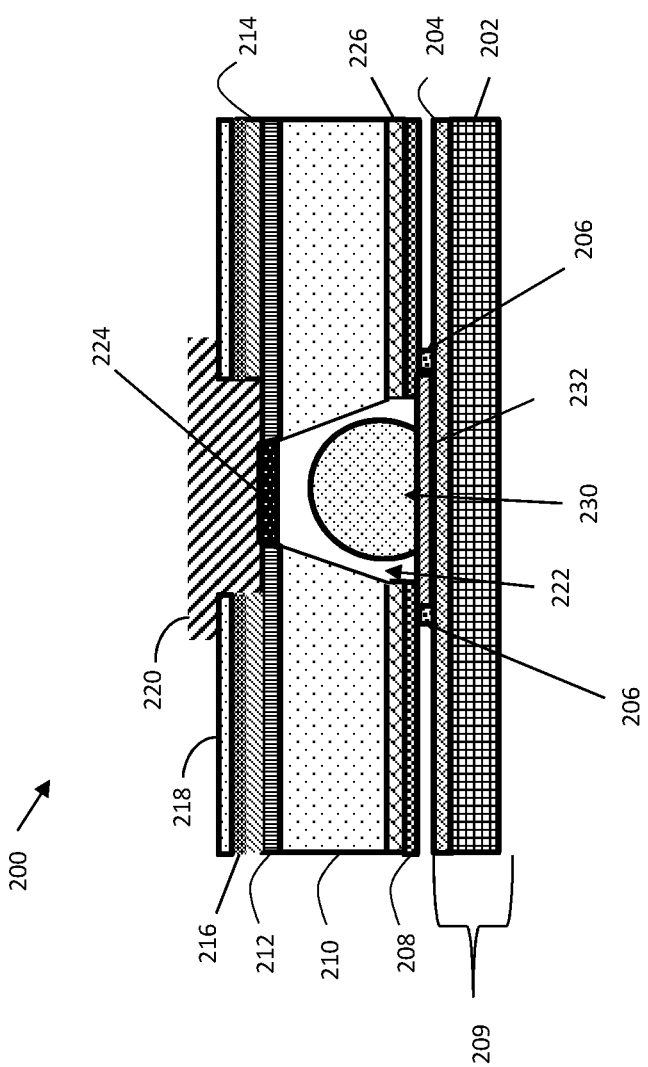
FIG. 3B depicts another view of the exemplary system of FIG. 3A according to one or more embodiments of the present invention.

FIG. 3B depicts the exemplary hydrophobic delivery system 200 of FIG. 3A after sealing the reservoir. The reservoir cavity 222 can be sealed with a second substrate 209. In some embodiments of the invention, the second substrate 209 can include a hydrophilic surface 232. For example, a hydrophilic surface 232 can attract the liquid in the reservoir 230, further drawing the liquid away from the membrane 220 and hydrophobic layer 224. The hydrophilic surface 232 can include any surface including a biocompatible material, including for instance materials commonly used in semiconductor devices, such as silicon (Si), $SiO_2$, $SiN_x$, or other oxides.

Figure 4A:
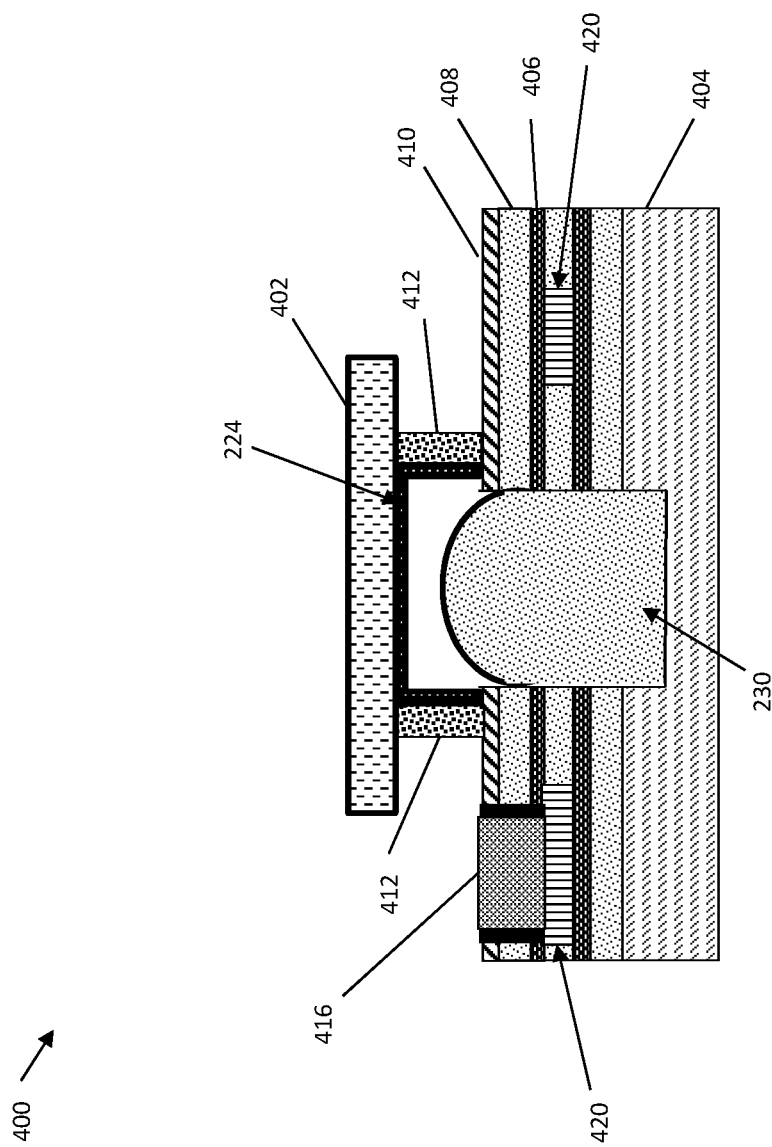
FIG. 4A depicts an exemplary system according to one or more embodiments of the present invention.

FIG. 4A depicts a hydrophobic delivery system 400 according to another embodiment of the invention. The system 400 includes a substrate 404 in which one or more cavities can be formed. The system 400 includes a hinged releasable membrane 402 connected to a hinged structure 412. The hinged structure can include a low melting point material, such as a metal coated polymer layer including In. The membrane, and optionally the handle or hinge 412, can be lined with a hydrophobic layer 224 on the interior of the reservoir. In some embodiments of the invention, a plurality of layers can be deposited or formed upon the substrate 40, such as oxide layers 408 and nitride layers 406. In some embodiments of the invention, the system 400 includes control circuitry. In some embodiments of the invention, the system 400 includes and a metal layer 410 in contact with the hinged structure 412. The system can also include electrode elements 420.

As is shown in FIG. 4A, a liquid 230 can be deposited in the reservoir and sealed with the membrane 402. Hydrophobic layer 224 can repel liquid in the reservoir 230 such that the liquid does not contact the membrane. The hydrophobic layer 224 can induce formation of an insulating air pocket between the surface of the liquid and the membrane 402.

Figure 4B:
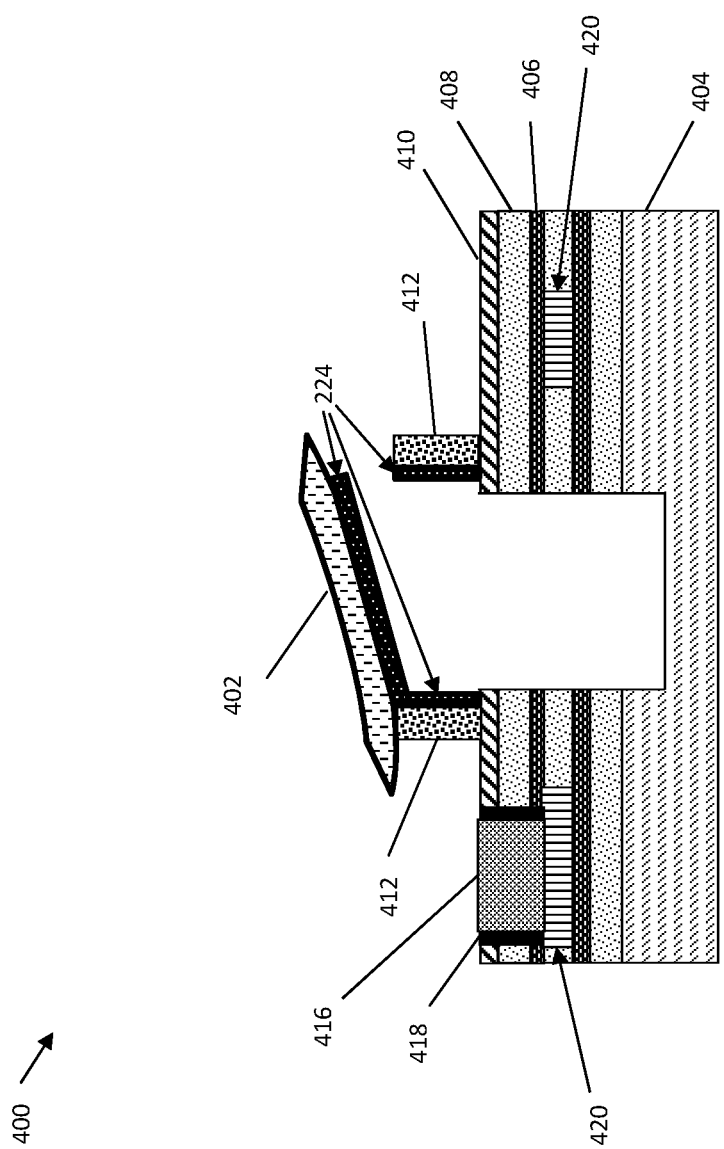
FIG. 4B depicts another view of the exemplary system of FIG. 3A according to one or more embodiments of the present invention.

FIG. 4B depicts the exemplary hydrophobic delivery system 400 of FIG. 4A after activation according to some embodiments of the invention. After activation, membrane 402 and at least a portion of hydrophobic layer 224 are partially released from the structure, for instance by microelectro-mechanical systems (MEMS) technology, exposing the reservoir to the local environment and allowing the release of substances inside the reservoir. For example, in some embodiments of the invention a hinge can be opened upon melting of a portion of a seal due to local heating by a connected electrode. In such embodiments of the invention, the membrane 402 can be opened to allow the rapid and complete release of substances within the reservoir without completely disconnecting the membrane from the delivery device. In some embodiments of the invention, the membrane 402 before activation is under mechanical stress and, for instance, can be relieved from such stress upon activation to facilitate opening of the membrane by curvature away from the reservoir cavity.

In the system of FIGS. 4A and 4B, for example, a melting temperature of about 157° C. can be required to open the reservoir for a membrane with dimensions of about 100 microns by 100 microns and having a thickness of about 1 micron including a seal composed of indium, corresponding to an energy of about 20 micro Joules ($\mu J$).

Structures according to FIGS. 4A and 4B can be fabricated by standard semiconductor fabrication techniques, including, for instance, damascene processes and standard lithography techniques used to fabricate multilayer CMOS structures.

Figure 5:
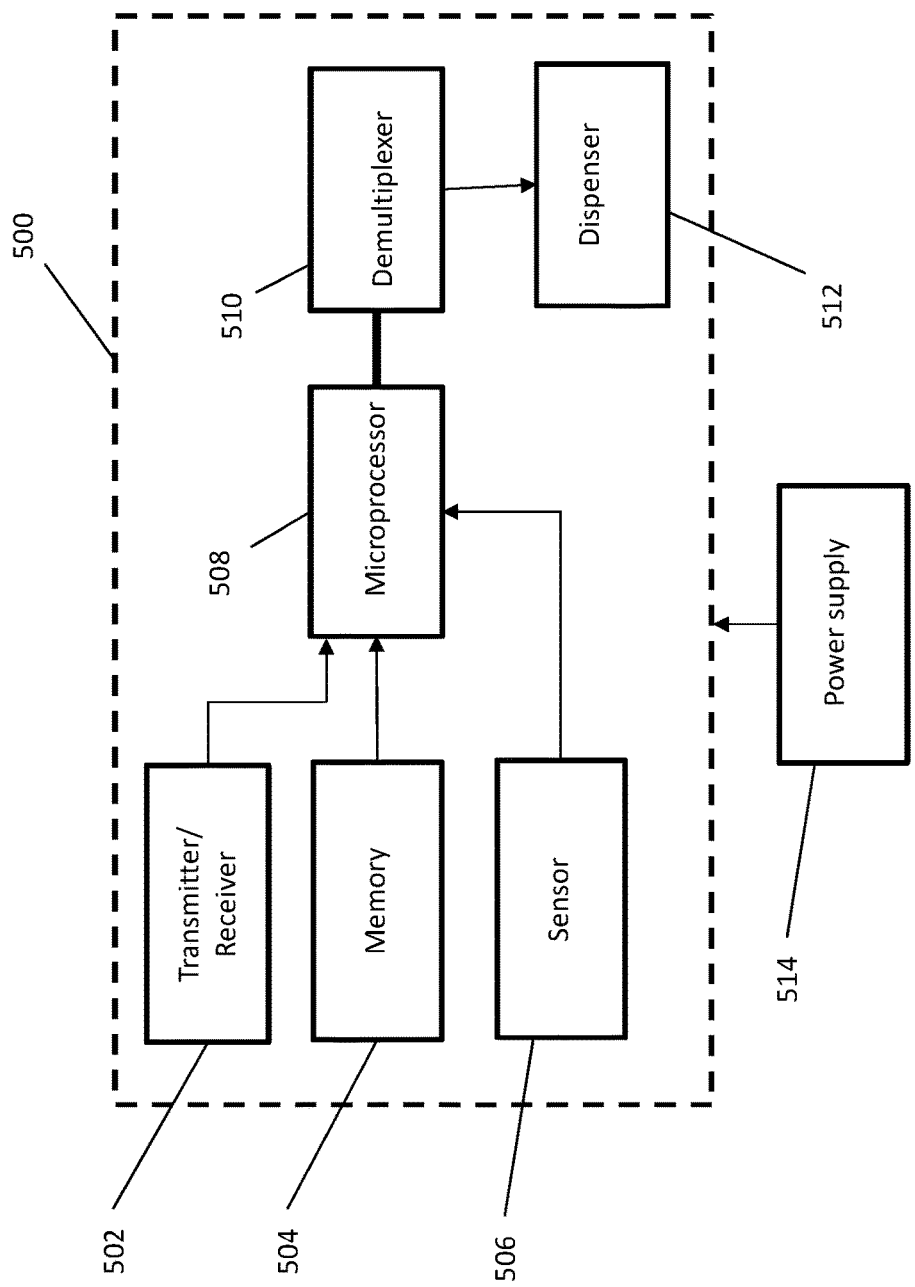
FIG. 5 depicts a block diagram of control circuitry according to one or more embodiments of the present invention.

FIG. 5 is a block diagram of control circuitry that can be configured to control the release of reservoir contents of a microchip substance delivery device, according to an embodiment of the invention. FIG. 5 depicts a control system 500 coupled to a power supply 514. The control system 500 can include a microprocessor 508, memory 504, such as a programmable ROM, one or more sensors 506, a wireless transmitter/receiver 502, a demultiplexer circuit 1510 and a dispensing array 512. Various components of the control system 500 include integrated circuits integrally formed as part of a delivery device including a hydrophobic layer. In FIG. 5, for example, the dispensing array 512 can include releasable membrane structures and reservoirs as discussed above. The control system 500 can be designed using standard circuit design methods and built with standard silicon integrated circuit technology.

The microprocessor 508 can generate control signals to the demultiplexer circuitry 510 to selectively activate one or more membranes of the dispensing array 512. In some embodiments of the invention, microprocessor 508 can generate control signals to activate substance release according to a programmed scheduled stored in the programmable ROM. In another embodiment of the invention, the microprocessor 508 can generate control signals to activate substance release according to control signals output from one or more sensors 506 that automatically detect when a substance is to be released according to local conditions. For instance, a delivery structure for pharmaceuticals can determine when doses of a given drug or medication are to be administered based at least in part on analysis of biosensor input, such as local pH or local ionic composition, and can activate of one or more membranes to release an active pharmaceutical ingredient from one or more reservoirs based at least in part on the sensed conditions. In yet another embodiment of the invention, the microprocessor 508 can generate control signals to activate substance release according to control signals output from a wireless receiver based at least in part on remote commands provided by a health care provider or individual having an implantable or wearable substance delivery device.

In some embodiments of the invention, the power supply 514 can be implemented as an internal power source, such as a bio-compatible thin-film battery, that is integrated with the microchip substance delivery device. For such embodiments of the invention, battery size, material, and packaging requirements limit the energy capacity, and it is for this reason that the energy requirements for substrate release are preferably minimized. In other embodiments of the invention, the power supply 514 can be implemented as a wireless power delivery system in which the power is transmitted to the control system 514 from an external source, such as by near field communication (NFC).

Figure 6:
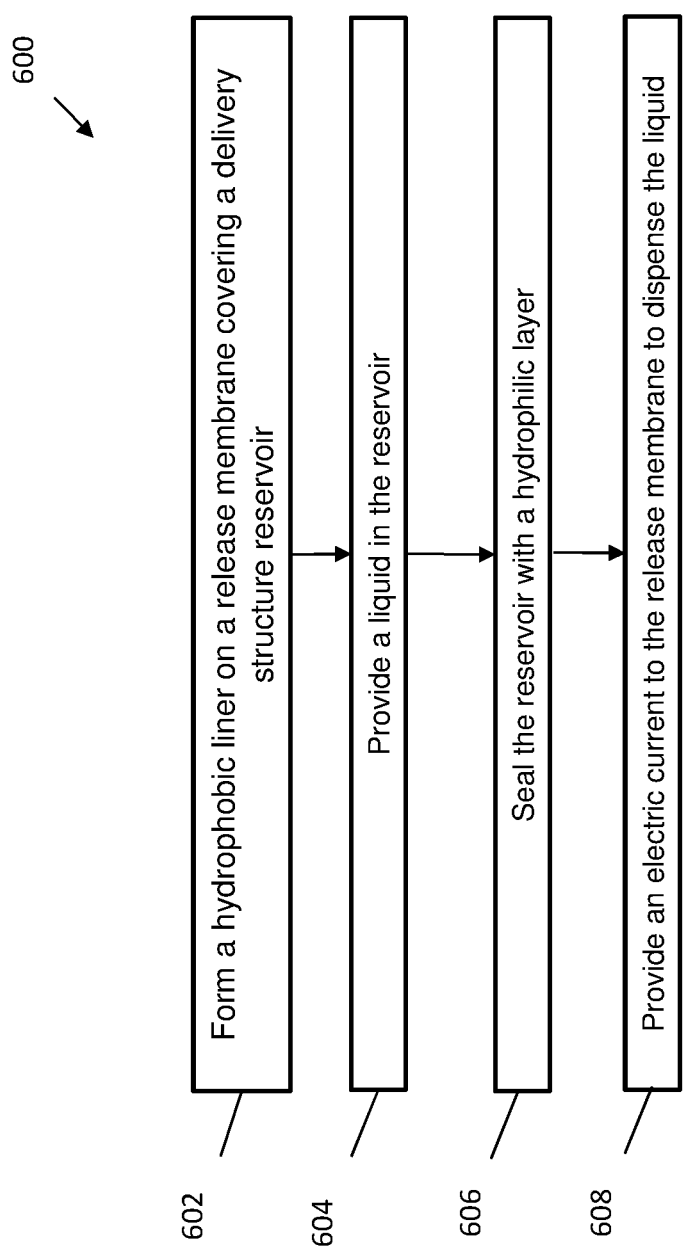
FIG. 6 depicts a flow diagram of an exemplary method according to one or more embodiments of the present invention.

FIG. 6 depicts a flow diagram of an exemplary method 600 of fluid delivery according to one or more embodiments of the present invention. The method 600 includes, for example, forming a hydrophobic liner on a release membrane in a delivery structure reservoir, as shown at block 602. The method 600 also includes providing a liquid in the reservoir, as shown at block 604. The method 600 also includes sealing the reservoir with a hydrophilic layer, as shown at block 606. The method 600 also includes providing an electric current to the release membrane to dispense the liquid, as shown at block 608.

Figure 7:
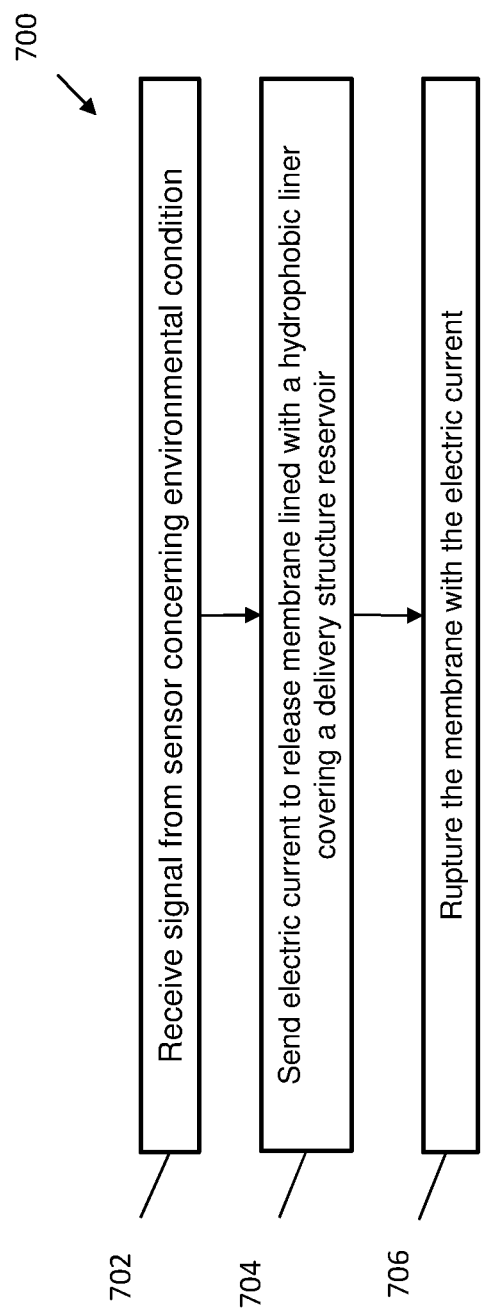
FIG. 7 depicts a flow diagram of an exemplary method according to one or more embodiments of the present invention.

FIG. 7 depicts a flow diagram of an exemplary method 700 of fluid delivery according to one or more embodiments of the present invention. The method 700 includes, for example, receiving a signal from a sensor concerning an environmental condition, as shown at block 702. Alternatively, in some embodiments of the invention (not illustrated in FIG. 7), the method can include receiving a signal from an external device or receiving a signal from a stored scheduling regimen. The method 700 also includes sending an electric current to a release membrane lined with a hydrophobic liner covering a delivery structure reservoir, as shown at block 704. The method 700 also includes rupturing the membrane with the electric current, as shown at block 706.

As used herein, "liquid" is understood to mean a fluid aqueous material. Liquids in embodiments of the invention can include any liquid suitable for delivery from a miniaturized delivery device. Liquids can include for example, but not by limitation, pharmaceutical solutions and preparations, nutritional solutions and preparations, nutraceutical solutions and preparations, catalysts, solvents, reagents, excipients, diluents, preservatives, and the like. In some embodiments of the invention, a reservoir includes one or more active pharmaceutical agents. In some embodiments of the invention, the reservoir includes an electrolyte, such as a microbattery electrolyte. In some embodiments of the invention, digital delivery devices are interfaced to sensor systems to provide an automatic closed-loop delivery systems In some embodiments of the invention, liquid delivery devices are included in implantable or wearable drug delivery systems. For example, liquid delivery devices can be included in systems directed to providing treatment and/or management of diabetes, pain, addiction, contraception, neurological disorders, or psychological disorders.

Embodiments of the invention can provide improved liquid delivery devices by providing decreased power consumption for the delivery of liquids in a miniaturized device. A hydrophobic layer adjacent the membrane can repel fluids from the membrane in the reservoir and thereby release materials from the structure with a lower energy expenditure.

Some embodiments of the invention provide improved liquid delivery devices by reducing the risk of destruction or degradation and/or increasing the integrity of liquids in the reservoir. A hydrophobic layer adjacent the membrane can repel fluids from the membrane in the reservoir and reduces the risk of damage to the fluids that would otherwise occur upon activation through passing an electric current through the membrane.

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

The phrase "selective to," such as, for example, "a first element selective to a second element," means that the first element can be etched and the second element can act as an etch stop.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

As previously noted herein, for the sake of brevity, conventional techniques related to semiconductor device and integrated circuit (IC) fabrication may or may not be described in detail herein. By way of background, however, a more general description of the semiconductor device fabrication processes that can be utilized in implementing one or more embodiments of the present invention will now be provided. Although specific fabrication operations used in implementing one or more embodiments of the present invention can be individually known, the described combination of operations and/or resulting structures of the present invention are unique. Thus, the unique combination of the operations described in connection with the fabrication of a semiconductor device according to the present invention utilize a variety of individually known physical and chemical processes performed on a semiconductor (e.g., silicon) substrate, some of which are described in the immediately following paragraphs.

In general, the various processes used to form a microchip that will be packaged into an IC fall into four general categories, namely, film deposition, removal/etching, semiconductor doping and patterning/lithography. Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others. Removal/etching is any process that removes material from the wafer. Examples include etch processes (either wet or dry), and chemical-mechanical planarization (CMP), and the like. Semiconductor doping is the modification of electrical properties by doping, for example, transistor sources and drains, generally by diffusion and/or by ion implantation. These doping processes are followed by furnace annealing or by rapid thermal annealing (RTA). Annealing serves to activate the implanted dopants. Films of both conductors (e.g., poly-silicon, aluminum, copper, etc.) and insulators (e.g., various forms of silicon dioxide, silicon nitride, etc.) are used to connect and isolate transistors and their components. Selective doping of various regions of the semiconductor substrate allows the conductivity of the substrate to be changed with the application of voltage. By creating structures of these various components, millions of transistors can be built and wired together to form the complex circuitry of a modern microelectronic device. Semiconductor lithography is the formation of three-dimensional relief images or patterns on the semiconductor substrate for subsequent transfer of the pattern to the substrate. In semiconductor lithography, the patterns are formed by a light sensitive polymer called a photo-resist. To build the complex structures that make up a transistor and the many wires that connect the millions of transistors of a circuit, lithography and etch pattern transfer steps are repeated multiple times. Each pattern being printed on the wafer is aligned to the previously formed patterns and slowly the conductors, insulators and selectively doped regions are built up to form the final device.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments of the invention, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments of the invention, the practical application or technical improvement over technologies found in the marketplace, or to enable others of ordinary skill in the art to understand the embodiments described herein.

What is claimed is:

1. A liquid delivery apparatus comprising:
   a first substrate comprising a reservoir formed in the first substrate;
   a membrane disposed on a first surface of the first substrate covering a first opening of the reservoir;
   a second substrate bonded to a second surface of the first substrate, wherein the second substrate comprises a reservoir seal covering a second opening of the reservoir, the reservoir seal comprising a hydrophilic surface;
   a hydrophobic layer disposed on an inside surface of the membrane;
   electrodes in electrical contact with the membrane; and
   a drop of solution disposed on the hydrophilic surface such that an air pocket is between the drop of solution and the hydrophobic layer.

2. The apparatus of claim 1, wherein at least a portion of the membrane comprises a metal film.

3. The apparatus of claim 1, wherein at least a portion of the membrane comprises an electrically-insulating film.

4. The apparatus of claim 1, wherein the reservoir seal comprises indium.

5. The apparatus of claim 1, wherein the hydrophobic layer comprises a fluorocarbon film.

6. The apparatus of claim 1 further comprising a sensor.

7. The apparatus of claim 1, wherein the hydrophobic layer comprises a porous electrodeposited metal film.

8. The apparatus of claim 1, wherein the hydrophobic layer has a thickness of about 5 Angstroms (Å) to about 1 micron.

9. The apparatus of claim 1 further comprising a liquid in the reservoir.

10. The apparatus of claim 9, wherein the liquid comprises an active pharmaceutical agent.

11. The apparatus of claim 8, wherein the liquid comprises a microbattery electrolyte.

12. The apparatus of claim 1, wherein the hydrophobic layer lines a portion of the cavity.

* * * * *